United States Patent [19]

Thornhill et al.

[11] Patent Number: 5,387,216
[45] Date of Patent: Feb. 7, 1995

[54] INTRAMEDULLARY BASED INSTRUMENT SYSTEMS FOR TOTAL KNEE REVISION

[76] Inventors: Thomas S. Thornhill, 8 Main St., Dover, Mass. 02030; Michael B. Martyn, 63 Circuit St., Norwell, Mass. 02061

[21] Appl. No.: 18,978

[22] Filed: Feb. 18, 1993

[51] Int. Cl.⁶ .............................................. A61F 5/04
[52] U.S. Cl. ...................................... 606/88; 606/86
[58] Field of Search ................... 606/62, 88, 87, 86, 606/89, 95, 99, 100, 79, 80, 82, 84, 85, 63, 64

[56] References Cited

U.S. PATENT DOCUMENTS

| | | | |
|---|---|---|---|
| 4,474,177 | 10/1984 | Whiteside | 606/88 |
| 4,487,203 | 12/1984 | Androphy | 606/88 |
| 5,002,545 | 3/1991 | Whiteside et al. | 606/80 |
| 5,037,423 | 8/1991 | Kenna | 606/88 |
| 5,053,037 | 10/1991 | Lackey | 606/79 |
| 5,098,437 | 3/1992 | Kashuba et al. | 606/89 |
| 5,234,433 | 10/1993 | Bert et al. | 606/88 |

FOREIGN PATENT DOCUMENTS 741869  6/1980  U.S.S.R. .................. 606/99

OTHER PUBLICATIONS

"EFTEKHAR II Knee Prosthesis" Technical Brochure, Howmedica, Inc. Rutherford, N.J. Date Unknown, Author unknown pp. 1–16.

*Primary Examiner*—Stephen C. Pellegrino
*Assistant Examiner*—Guy V. Tucker
*Attorney, Agent, or Firm*—Joseph F. Shirtz

[57] ABSTRACT

Instrumentation useful in knee revision surgery uses the intramedullary canal as a mount for other instruments, such as cutting guides. A bearing sleeve is inserted into the intramedullary canal by a rod. The position of the rod within the sleeve and the canal is then fixed and a cutting guide is attached to the proximal end of the rod. The rod and sleeve connection prevents abandonment of the sleeve in the canal.

5 Claims, 4 Drawing Sheets

INTRAMEDULLARY BASED INSTRUMENT SYSTEMS FOR TOTAL KNEE REVISION

BACKGROUND OF THE INVENTION

1. Field of the Invention

This invention relates to instruments for use in surgery and in particular, instruments for use in knee replacement surgery for preparation of bone tissue for receipt of joint prosthesis.

2. Background

It has long been known that implants may be devised which can be used to replace the natural joints provided in the mamillian body. In particular knee and hip replacements in humans is becoming more common. As these operations become more common, the need to replace worn out, old implants with newer or stronger implants or to readdress a progressive bone disease is on the upswing.

When performing, for example, knee revision surgery, a substantial portion of the bone at the distal end of the femoral bone and the proximal end of the tibial bone is removed. The removed bone makes way for the portion taken up by the new implant which is inserted into and fixed to the bone. This fixed implant is then received within the body to act as a replacement for the removed bone tissue.

Occasionally, it becomes necessary to replace a previously implanted prosthesis with a new prosthesis. In performing the replacement or revision surgery, it is necessary to remove the old prosthesis, either due to the continued disease of the bone or failure of the prosthesis itself.

In revision surgery, that is surgery where a new prosthesis is being implanted in the place of an old prosthesis, a substantial additional quantity of bone is removed. Often the removal of the implant itself destroys much of the bone tissue which surrounds the mounting site of the implant or the disease has advanced to such a state as to require a large amount of bone removal, both internal to the bone itself and along the distal or proximal portions as the case may be.

In performing this revision type of surgery, the removal of the old prosthesis and the large volume which is devoid of supporting bone attendant with the implant removal, creates a situation where it is difficult to provide sufficient mounting for the instruments necessary to make the accurate cuts needed for the new implant. That is, there is not a sufficient anchor site to provide positioning for the instrumentation in order to make accurate and complete cuts.

SUMMARY OF THE INVENTION

The present invention provides for improved instrumentation which can be used in knee revision surgery in order to provide a strong and accurate mount for the instrumentation in situations where substantial quantities of bone have been removed from the mounting site.

In particular, the invention calls for a bearing sleeve, which is inserted into the severely damaged canal in order to take up the additional volume. A rod is passed through the sleeve and may be positioned at a point extended further into the bone such that it meets with the natural canal of the bone to provide a second mounting site. This rod is then held in a relatively fixed position by the interaction of the holding force of the canal and the holding force of the bearing sleeve. A cutting guide may then be mounted at the proximal end of the rod to position the saw for cuts to be made to the bone material to remove diseased bone and provide an appropriate mounting surface for the new revision implant.

The instrumentation also provides a novel set up which prevents the removal of the rod from the intramedullary canal of the bone without the attendant removal of the bearing sleeve. This prevents the unwanted abandonment of the sleeve within the bone canal.

The rod is adapted to receive on its proximal end a handle which assists in inserting the rod into the intramedullary canal as well as withdraw of the rod at the end of the procedure. The handle is removalable in order to make room for the cutting blocks or guides which are received on the rod in order to make the appropriate bone cuts for receipt of the implant.

BRIEF DESCRIPTION OF THE FIGURES

Description of the invention will be given with references to the attached figures wholein.

DETAILED DESCRIPTION OF THE PREFERRED EMBODIMENT

Figure 1:
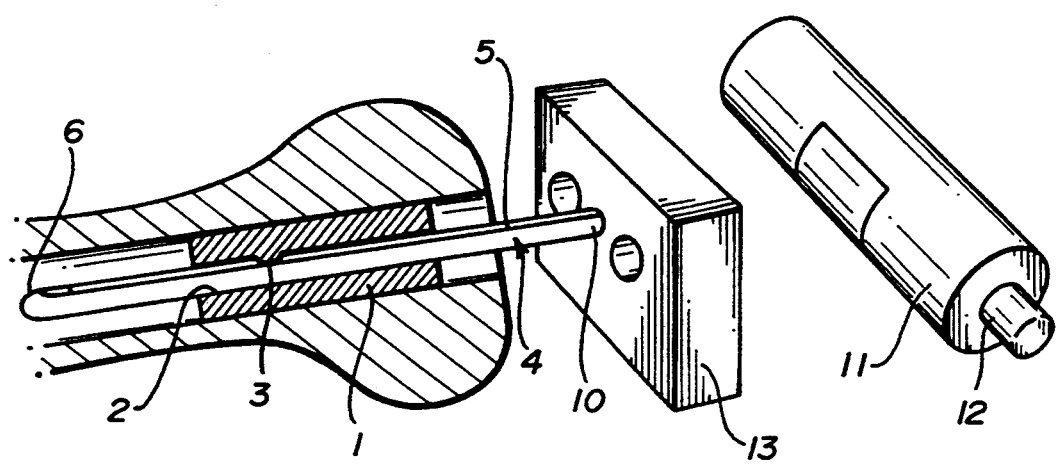
FIG. 1 is a schematic view of the instrument in surgical position.
Figure 2:
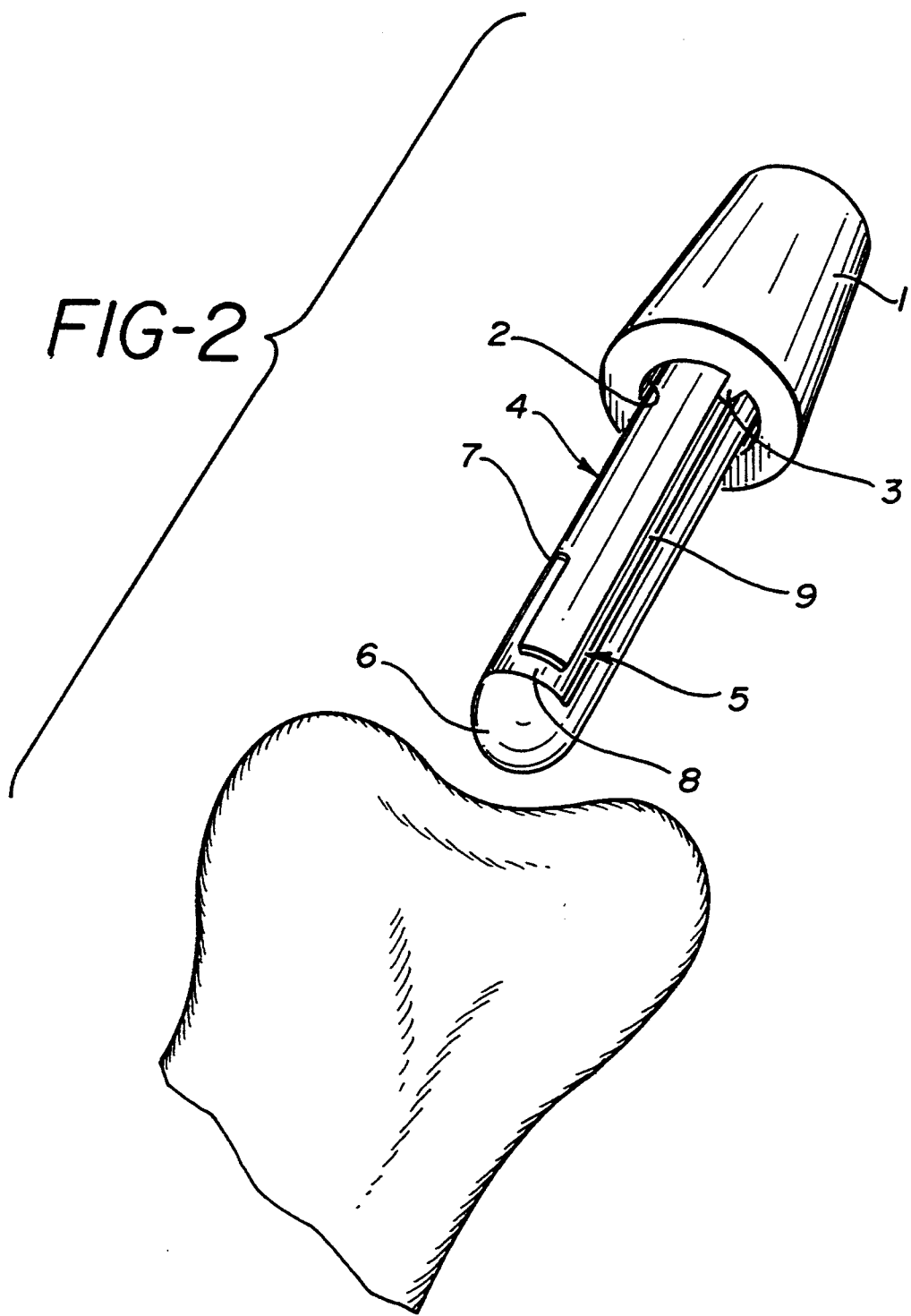
FIG. 2 is a perspective view of the distal end of the instrument.
Figure 3:
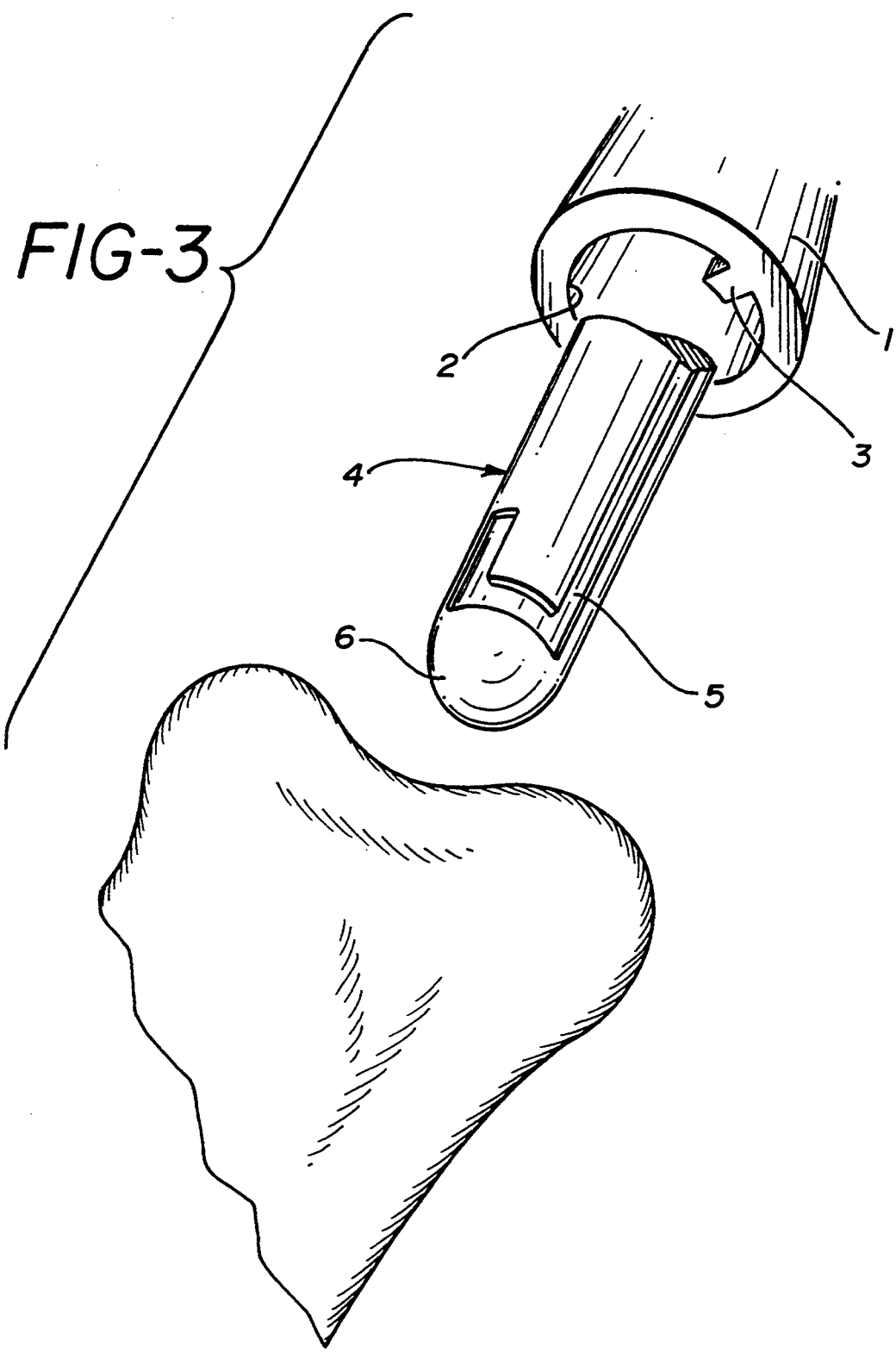
FIG. 3 is a further view of the distal end of the instrument.
Figure 4:
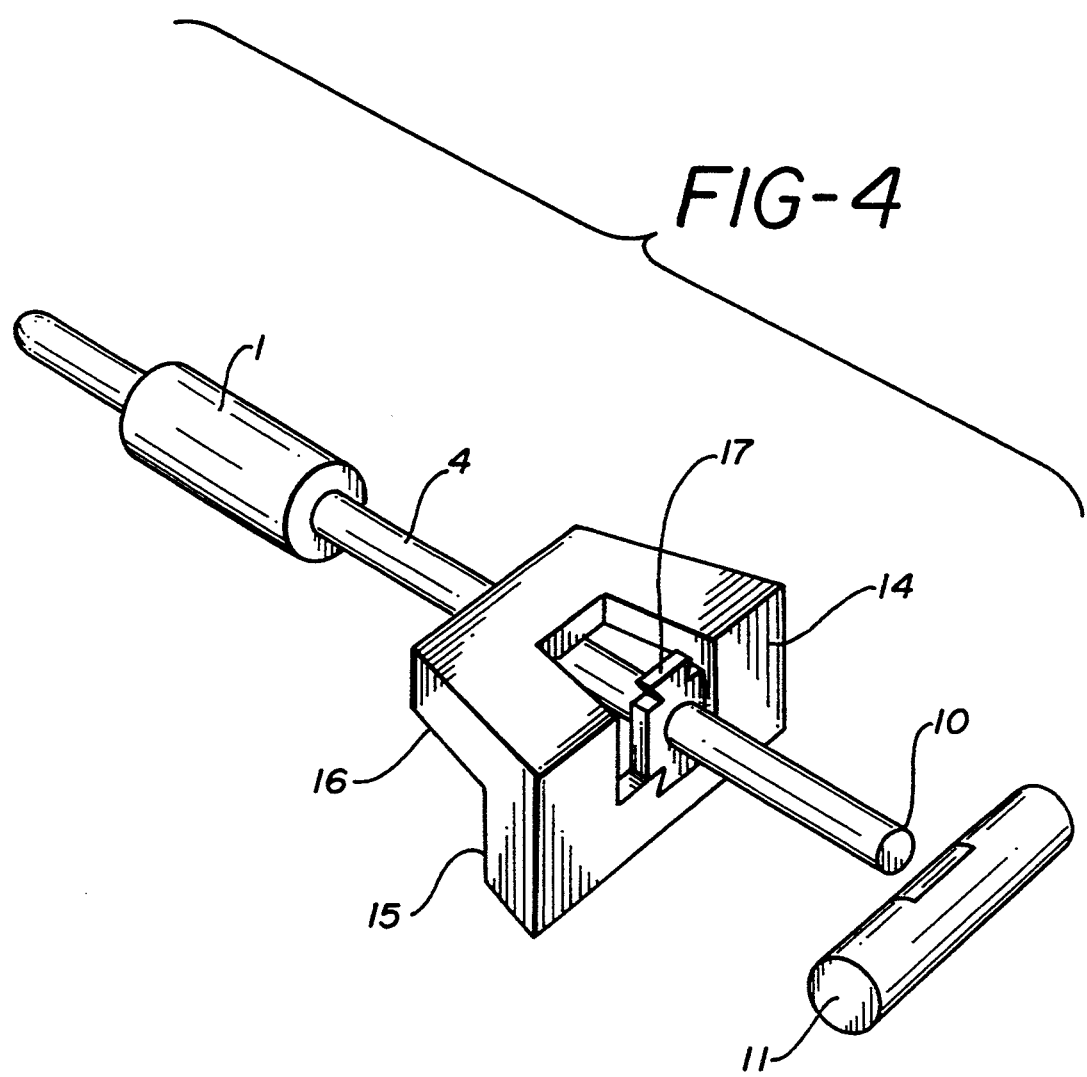
FIG. 4 is a view of an alternative embodiment.

Referring to FIG. 1 there is shown a bearing sleeve 1 which is made of an appropriate medical grade material for receipt within the intramedullary canal of a bone. The sleeve defines a central bore 2 extending longitudinally through the sleeve, providing communication from one end of the sleeve to the other. A small protrusion or follower 3 is formed on the surface defining the central bore 2. The use of this follower will be described below in connection with the explanation of rod 4. The sleeve may be substantially cylindrical in shape or have a slight taper in order to provide for a snug fit within a largely diseased bone, having a tapered void.

The rod 4 is received within the opening of the bearing sleeve 1. This rod has a track 5 defined in the outer surface thereof in the form of an open slot. The slot receives the follower 3 in order to position the sleeve and rod with respect to one another to a certain degree. The track extends to the distal end 6 of the rod and terminates in a blind portion 7. This blind portion is merely an extension of the track which extends back towards the proximal end of the rod. The blind portion is connected at one end to a transverse portion 8 in communication for receipt of the follower. The transverse portion 8 in turn communicates with a longitudinal portion 9, which extends the length of the rod to the proximal end 10. In this manner, the sleeve and rod may be assembled by the insertion of the rod into the sleeve from the proximal end of the rod. The follower 3 is received within the longitudinal portion 9 of the track 5. The sleeve is then moved longitudinally along the length of the rod until the follower reaches the end of the longitudinal portion 9 at which point a twisting of the rod moves the follower into the transverse portion 8 of the rod. Once in this position the sleeve is fixed relative to longitudinal movement of the rod. That is, longitudinal movement of the rod will impart a force to the sleeve for insertion within the intramedullary canal of the bone or later removal of the sleeve from the intramedullary canal. It is also easily seen that the sleeve is not fixed relative to rotational movement of the rod so that the follower may be positioned alternatively in either longitudinal portion 9 or blind portion 7 of the track 5.

A detachable handle 11 is then positioned and attached to the proximal end 10 of the rod. The rod and sleeve assembly is inserted into the intramedullary canal of the patient using the rod and handle as a guide for the sleeve. Once within the intramedullary canal, force is applied to the handle in order to securely seat the sleeve within the intramedullary canal of the patient. This force may be applied with the follower either in the blind portion 7 or in the transverse portion 8 of the rod. Preferably, the follower is positioned in the blind portion 7 in order or provide greater stability to the system.

Once the sleeve is firmly seated within the intermedulary canal, the follower is moved from its position either in the transverse portion 8 of the track or in the blind portion 7 of the track 5 to a position within the longitudinal portion 9 of the track 5. In this position the follower does not prevent the longitudinal motion of the rod farther into the intermedulary canal of the patient. The rod then slides through the bearing into the intermedulary canal of the patient until sufficient resistance from the natural canal is provided to the rod in order to seat the rod and bearing assembly in a secure fashion. In order to facilitate this insertion, the distal end of the rod may be tapered slightly in order to provide a clearing function as it is inserted further into the intramedullary canal.

At this point it is easily seen that the sleeve can only be fed onto the rod from the handle end of the rod, that is from the proximal end 10 of the rod. The follower prevents the removal of the sleeve from the distal end of the rod through it cooperation and interference within the track 5 of the rod. The rod sleeve assembly cannot be introduced handle first as the sleeve would merely slide along the rod and not be forced into the intramedullary canal as is necessary for proper seating. The follower prevents removal of the sleeve from the distal end and requires removal of the sleeve from the proximal end 10 of the rod 4. That is the sleeve can only be removed from the rod in a direction away from the intermedulary canal of the patient.

The detachable handle 11 has a push button 12 which operates to release the handle from the rod 4. The push button operates an appropriate locking mechanism within the handle which locks the handle to the end of the rod 4. This locking mechanism is spring biased such that insertion of the rod into the handle, locks the rod to the handle and only upon the depression of the push button 12 does the locking mechanism release the rod from the handle.

An example of a sleeve for use in the femoral portion of the instrumention may be made of stainless steal having a longitudinal length of approximately 4 inches with an opening formed through the surface at a position approximately 2 inches from one end for receipt of a small post which forms the follower. The post may be welded to the sleeve once positioned such that one end extends into the internal portion of the sleeve. Alternatively, the post may be press fit into the sleeve opening of the such that one end extends into the central bore 2. The sleeve may have a diameter 0.610 inches for a 16 mm sleeve and an internal diameter of 0.315 inches. The rod is made out of a surgical grade of stainless steel and may, for example, be a 300 mm size, having a length of 12.00 inches overall. The rod may have a diameter, which is preferred to be approximately 0.312 inches. Thus it is easily seen that the rod will slide easily within the central board 4 of the previously described sleeve.

The slot is formed along the length of the rod extending all the way from the proximal end of the rod to a position approximately 0.930 inches from the distal end. At this point it turns and passes around the circumference of the rod to a position diametrically opposite the position of the longitudinal portion of the slot. There the slot turns back along the longitudinal direction toward the proximal end of the rod and extends along the length approximately 1.139 inches. A small cut-out or transfer for receiving the handle is formed on the proximal end in order to facilitate insertion of the rod into the handle and secure mounting therein.

Once positioned, the handle is removed from the rod and a sizing cutting block assembly 13 is received thereon. The cutting block 13 is particular to the type of implant being used. That is different implants require cuts of different size and shape and therefor the specifics of the cutting guide will not be described herein as they are implants specific. The cutting block may either be mounted on the end of the rod 4 in the same formation used to attach the handle 11 or may merely receive the rod within an opening defined on the cutting block for positioning along the length of the rod. Rotational position of the cutting block is then determined using a normal surgical technique. In this situation, openings are formed in the cutting block in order to receive pins, which pin the position of the cutting guide with respect to the bone being adapted in order to prevent rotation movement of the cutting guide on the rod. The rod, through the anchoring of the distal end within the intramedullary canal and the sleeve, provides strong forces for maintaining the transverse position of the guide. Therefore, the pins need merely be strong enough to maintain the rotational position of the cutting guide.

A notch guide 14 may also be received on the rod independent of the cutting guide. This guide 14 has a surface portion 15 and a face portion 16 for mating with the end of the bone. In this portion of the apparatus, the notch guide may be received directly on the rod and a detachable handle attached to the guide itself. The sleeve and rod are inserted as described above but only to a position where the surface portion 15 of the notch guide rests securely on the end of the bone in the position necessary for appropriate cuts. The handle may then be moved providing freedom of movement for the surgeon in order to appropriately position the saw along the notch guide to make appropriate cuts.

The notch guide may be provided with an appropriate dovetail set up which mates with an appropriate dovetail on the detachable handle used for the notch guide. Either the handle or the notch may have a pin of the dovetail 17 while the other would have the tail. Preferably, however, the tail is formed in the notch as this provides more open space for movement of the saw.

The invention has been described by reference to its preferred embodiment. However, the scope of the invention is set out in connection with the following claims. It may easily be seen that alternatives to the preferred embodiment may be made while still within the scope and breadth of the spirit of the invention.

We claim:

1. An instrument for use in preparing bone for receipt of a prosthesis comprising:
   a) a rod having a longitudinal length, a distal end and a proximal end and a pre-determined diameter;
   b) a slot formed in the outer surface of said rod and extending along the longitudinal length of said rod from the proximal end to a position near the distal end and terminating short of the distal end of said rod at a slot distal end, and at the distal end of said slot, said slot extends transversely about the circumference of said rod to a position approximately opposite the longitudinally extending portion of said slot and then extends along a pre-determined length back towards the proximal end of said rod;
   c) a bearing having pre-determined outer diameter and defining an inner bore of predetermined diameter for receipt of said rod;
   d) a follower formed on the inner surface of said bearing for receipt within the slot of said rod for guiding said bearing along the length of said rod.

2. The instrument according to claim 1 further including a detachable handle for receipt on the proximal end of said rod.

3. The instrument according to claim 2 wherein said handle has means for firmly attaching said handle to said proximal end and selectively removing said handle from said proximal end.

4. An improved instrument for use in prosthetic implant surgery comprising a longitudinally extending rod for receipt within an intramedullary canal of an appropriate long bone of a mammal, which bone is to receive a portion of a prosthesis the improvement comprising:
   a) means on said rod for guiding a bearing sleeve along the length of said rod;
   b) a bearing sleeve for receipt within a portion of the intramedullary canal of said long bone, said bearing sleeve defining an inner bore for receiving said rod therein;
   c) means for holding said sleeve in a first predetermined position against relative longitudinal movement of said rod for fixation or removal of said sleeve within the intramedullary canal, and
   d) a cutting block defining means for receiving said rod to position said cutting block in a predetermined position for providing a guide to other instruments used in the surgery.

5. An instrument according to claim 4 further including means for removing said rod and sleeve from the intramedullary canal after placement of said cutting block without removal of said cutting block from said bone.

* * * * *